(12) United States Patent
Moszner et al.

(10) Patent No.: US 8,557,888 B2
(45) Date of Patent: Oct. 15, 2013

(54) POLYMERIZABLE COMPOSITIONS WITH IMPROVED THROUGH-CURING DEPTH

(75) Inventors: Norbert Moszner, Mauren (LI); Ulrich Salz, Lindau (DE); Peter Burtscher, Rankweil (AT); Robert Liska, Schleinbach (AT); Astrid Gugg, Vienna (AT); Christian Gorsche, Vienna (AT)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 13/295,362

(22) Filed: Nov. 14, 2011

(65) Prior Publication Data

US 2012/0302657 A1 Nov. 29, 2012

(30) Foreign Application Priority Data

Nov. 19, 2010 (EP) ..................................... 10191957

(51) Int. Cl.
*C08F 2/50* (2006.01)
*C08B 37/00* (2006.01)
*B29C 71/04* (2006.01)
*H05B 6/68* (2006.01)
*C08G 61/04* (2006.01)

(52) U.S. Cl.
USPC ............ 522/24; 522/7; 522/6; 522/71; 522/1; 520/1

(58) Field of Classification Search
USPC .............................. 522/124, 7, 6, 71, 1; 520/1
See application file for complete search history.

(56) References Cited

U.S. PATENT DOCUMENTS

| 4,222,835 A * | 9/1980 | Dixon ............................... 522/13 |
| 6,057,406 A | 5/2000 | Pojman et al. |
| 6,242,525 B1 * | 6/2001 | Raetzsch et al. ............... 524/525 |
| 6,313,237 B1 | 11/2001 | Pojman et al. |
| 6,533,503 B2 * | 3/2003 | Pfeil et al. ................... 405/259.5 |
| 6,852,775 B1 | 2/2005 | Soglowek et al. |
| 2001/0016628 A1 | 8/2001 | Raetzsch et al. |
| 2003/0158288 A1 | 8/2003 | Lehmann et al. |
| 2009/0239967 A1 * | 9/2009 | Moszner et al. ................ 522/66 |
| 2010/0292410 A1 | 11/2010 | Doshev et al. |

FOREIGN PATENT DOCUMENTS

| GB | 1041088 | 9/1966 |
| JP | 61-203109 | 9/1986 |
| JP | 2007034063 | 2/2007 |
| SU | 238779 | 8/1973 |
| WO | 2010067790 | 6/2010 |

OTHER PUBLICATIONS

Khan et al., Trends in Polymer Science, 4 (1996) 253-257.
Washington et al., Polymer News, 2003, vol. 28, 303-310.
Nason et al., Macromolecules 38 (2005) 5506-5512.
Fouassier et al., Photoinitiation, Photopolymerization and Photocuring, Hanser Publishers, Munich, Vienna, New York, 1995, 22 et seq.
Fouassier et al., Radiation Curing in Polymer Science and Technology, vol. III, Elsevier Applied Science, London and New York 1993, 189 et. seq.
Fouassier et al., Radiation Curing in Polymer Science and Technology, vol. III, Elsevier Applied Science, London and New York 1993, 228 et seq.
Webster et al., A Compilation of Oligomers and Monomers Commercially Available for UV Today, SITA Technology, London (2001).
Warren et al., "Solution of a field theory model of frontal photopolymerization", Physical Review, E72, 2005.
EP application 10191957.9, European Examination Report, Feb. 19, 2013.
JP application 2011-246447, Office Action, dated Feb. 18, 2013.

* cited by examiner

*Primary Examiner* — Ling Choi
*Assistant Examiner* — Jessica E Whiteley
(74) *Attorney, Agent, or Firm* — Ann M. Knab; Thad McMurray

(57) ABSTRACT

Composition which contains polymerizable binder and an initiator according to the following Formula I:

$$R^1-X-O-O-[Y-O-O-]_n R^2 \qquad \text{(Formula I)}$$

and having a large through-curing depth and a sufficiently long processing time and which cures without the development of high temperatures.

12 Claims, No Drawings

POLYMERIZABLE COMPOSITIONS WITH IMPROVED THROUGH-CURING DEPTH

CROSS-REFERENCE TO RELATED APPLICATIONS

This application claims the benefit of European Patent Application No. 10191957.9 filed Nov. 19, 2010, which is hereby incorporated by reference in its entirety.

TECHNICAL FIELD

The present invention relates to polymerizable compositions which are particularly suitable as dental materials, such as prosthesis materials, materials for inlays, onlays, crowns or bridges as well as fillings.

BACKGROUND

Various polymerization mechanisms are used for curing polymerizable materials such as dental materials. For materials which are based on (meth)acrylates, the curing takes place via a radical polymerization, wherein radical formation and thus curing can be initiated thermally, chemically, or by light. Thermal curing is used predominantly for prosthesis materials, but does not come into consideration for a curing under oral conditions. The redox initiator systems used for chemical initiation consist at least of two components, usually a peroxide and a reductant. Due to the high reaction rate of peroxide and reductant, the two components may be combined only shortly before the curing of the dental material, and only a short processing time is available. Moreover, in the case of highly-filled filling composites in particular, it is possible only with difficulty to mix the so-called initiator paste with the accelerator paste without introducing air bubbles, with the result that photoinitiators are mainly used for this. A further disadvantage is the poor storage stability of peroxides used as initiators. A major disadvantage of light-curing dental materials is the limited through-curing depth, in particular of pigmented composites, with the result that they must be cured in layers, which is time-consuming.

In so-called frontal polymerization (FP), a reaction zone is produced which goes from the sample surface through the whole reaction mixture and thus results in a polymerized product. A. Khan, J. A. Pojman, Trends in Polymer Science, 4 (1996) 253-257, describe the frontal polymerization of n-butyl acrylate, in which the reaction is started on the surface by heat. The reaction heat produced during the polymerization of the surface layer triggers the polymerization in the adjacent layer, and a polymerization front thus forms which goes through a polymerization mixture at a rate of approximately 1 cm per minute. Temperatures of up to 290° C. are reached in the reaction zone. As the high temperatures can lead to the evaporation of the monomers and thus to blistering, the reaction is carried out under a pressure of >15×10$^5$ Pa.

According to Washington and Steinbock, Polymer News, 2003, Vol. 28, 303-310, high temperatures can lead to a decomposition of the initiator ("initiator burnout") and thus stop the polymerization front.

Nason et al., Macromolecules 38 (2005) 5506-5512, disclose the UV-light-induced frontal polymerization of multifunctional (meth)acrylates. At the polymerization front, temperatures of over 200° C. were measured which are not suitable for intraoral dental use.

U.S. Pat. No. 4,222,835, which is hereby incorporated by reference in its entirety, discloses compositions curable by frontal polymerization which are intended to be suitable for coating glass fibres or other objects.

U.S. Pat. Nos. 6,057,406 and 6,313,237, which are hereby incorporated by reference in their entirety, disclose the production of polymeric gradient materials by thermally initiated frontal polymerization.

A mortar curable by frontal polymerization which is intended to be suitable in particular for fastening tie bars and reinforcing iron in boreholes is known from U.S. Pat. No. 6,533,503, which is hereby incorporated by reference in its entirety.

SUMMARY

The object of the invention is to provide materials and in particular dental materials with large through-curing depth which do not have the above disadvantages and which have in particular a sufficiently long processing time and which cure without the development of high temperatures.

DETAILED DESCRIPTION

This object is achieved according to the invention by compositions which contain, in addition to a polymerizable binder, at least one initiator according to the following Formula I:

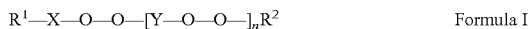

$$R^1-X-O-O-[Y-O-O-]_n R^2 \qquad \text{Formula I}$$

in which
$R^1$=is H, a linear, branched or cyclic aliphatic $C_1$-$C_{20}$ radical, which can contain one or more multiple bonds and/or one or more heteroatoms selected from O, S and —NR$^5$—, an aromatic $C_6$-$C_{24}$ radical or a combination of one such aliphatic and one such aromatic radical or has one of the meanings given for $R^2$;
$R^5$=is H, phenyl or $C_2$-$C_9$ alkyl;
X is —CO— or is absent;
$R^2$=is —CO-M, —SO$_2$-M or —P(=O)(-M)(—R$^3$);
$R^3$=is R', —OR' or —OO(CO)$_m$R', wherein R' is H, a linear, branched or cyclic aliphatic $C_1$-$C_{20}$ radical, which can contain one or more multiple bonds and/or one or more heteroatoms selected from O, S and N, an aromatic $C_6$-$C_{14}$ radical or a combination of one such aliphatic and one such aromatic radical, and m is 0 or 1;
M is —CH=CH$_2$ or —C(R$^4$)=CH$_2$;
  $R^4$=is a $C_1$-$C_{10}$ alkyl radical or a $C_3$-$C_8$ cycloalkyl radical, wherein these radicals can contain one or more S or O atoms, a phenyl radical or benzyl radical, wherein the named radicals can be halogenated and in particular fluorinated or perfluorinated, —F, —Cl or —Br;
Y is a bivalent, linear, branched or cyclic aliphatic $C_1$-$C_8$ radical; and
n=is 0, 1 or 2.

Formula I covers only those compounds which are compatible with the theory of chemical valence.

Preferred are compounds according to Formula I in which at least one of the variables has one of the following meanings:

$R^1$=is H, a linear, branched or cyclic aliphatic $C_1$-$C_6$ radical, which can contain a multiple bond and/or one or more heteroatoms selected from O and S, an aromatic $C_6$-$C_{10}$ radical or a combination of one such aliphatic and one such aromatic radical or has one of the meanings given for $R^2$, preferably a branched aliphatic $C_3$-$C_6$ radical or cumyl radical;

X=is —CO— or dispensed with, preferably dispensed with;

$R^2=$ is —CO-M, —SO$_2$-M or —P(=O)(-M)(—R$^3$), preferably —CO-M or —P(=O)(-M)(—R$^3$);

$R^3=$ is R', —OR' or —OO(CO)$_m$R', wherein R' is H, a linear, branched or cyclic aliphatic C$_1$-C$_6$ radical, an aromatic C$_6$-C$_{10}$ radical or a combination of one such aliphatic and one such aromatic radical, and m is 0 or 1, preferably R' or OR', wherein R' is a linear or branched C$_1$-C$_6$ radical;

M= is —CH=CH$_2$ or —C(R$^4$)=CH$_2$, in particular —CH=CH$_2$;

$R^4=$ is a C$_1$-C$_2$ alkyl radical, —F, —Cl, —Br, —CF$_3$ or a phenyl radical, preferably —CH$_3$, —CF$_3$ or F;

Y= is a bivalent, linear, branched or cyclic aliphatic C$_1$-C$_8$ radical, preferably a branched C$_6$-C$_8$ radical; and n= is 0, 1 or 2, preferably 0 or 1.

The compounds of Formula (I) are polymerizable peroxide initiators. It is assumed that, when polymerized, these compounds, through the addition of radicals, produce peroxide species which decompose at a lower temperature and thus make it possible to reduce the polymerization front temperature. Here, this procedure is called radical-induced destabilization. The destabilization is probably due to the increase in the degree of branching. Through the addition of a radical to the double bond of the group M, a radical forms which can add a further monomer molecule and thereby increases the degree of branching at the C atom adjacent to the CO group. For example, during the addition of the radical .R to the double bond of tert.-butyl peracrylate and the further addition of a monomer molecule vinyl-Z to the radical formed, a more strongly branched species forms (cf. structure in the dotted box) which is similar to the structure of the isobutyric acid-tert.-butyl ester:

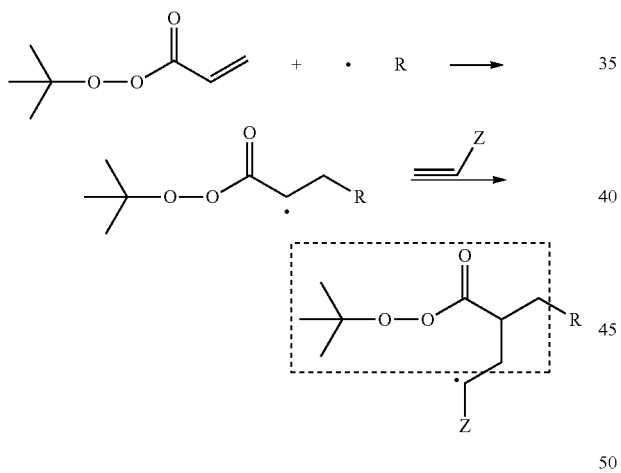

This species is more easily thermally splittable due to the increased degree of branching compared with the tert.-butyl peracrylate used, and thus allows a reduction in the polymerization front temperature. The compositions according to the invention are characterized in that they contain initiators of Formula I, and can therefore be cured by frontal polymerization at relatively low front temperatures. This has the advantage that a boiling of monomers and thus a blistering, which can result in inhomogeneities and instability, is avoided. The application of above-atmospheric pressure during polymerization is not required. In addition, a decomposition of initiators is avoided as a result of the low polymerization front temperature and a stable polymerization front achieved.

The initiators according to Formula I are relatively easily accessible. The synthesis of the initiators can be carried out e.g. by reaction of known hydroperoxides with unsaturated acid halides.

General:

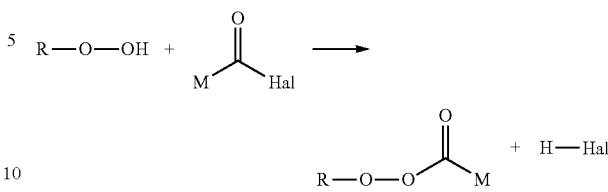

Specific Example:

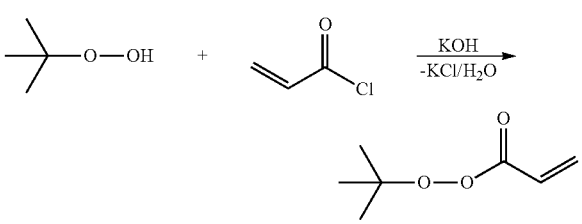

Starting from hydrogen peroxide as per compound, initiators with a symmetric structure can be obtained:

Specific Example:

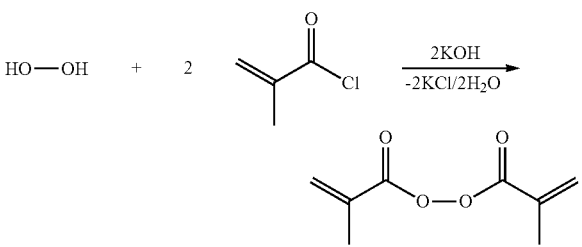

Preferred examples of the initiators according to the invention according to Formula I are in particular:

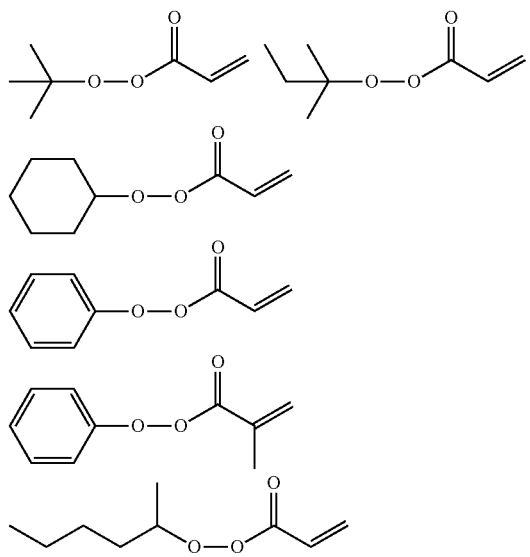

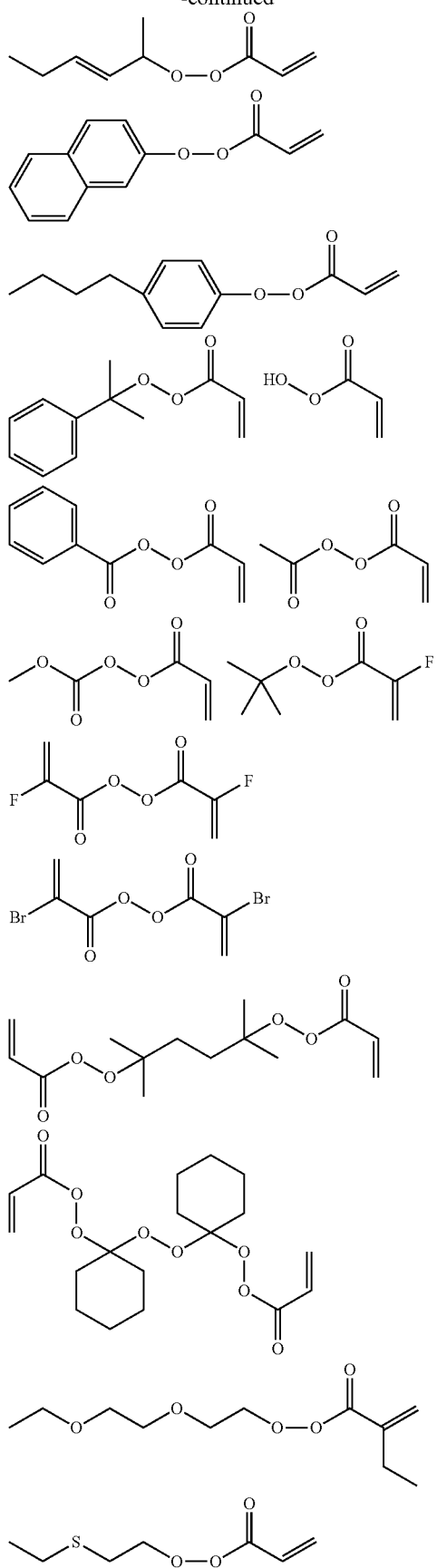
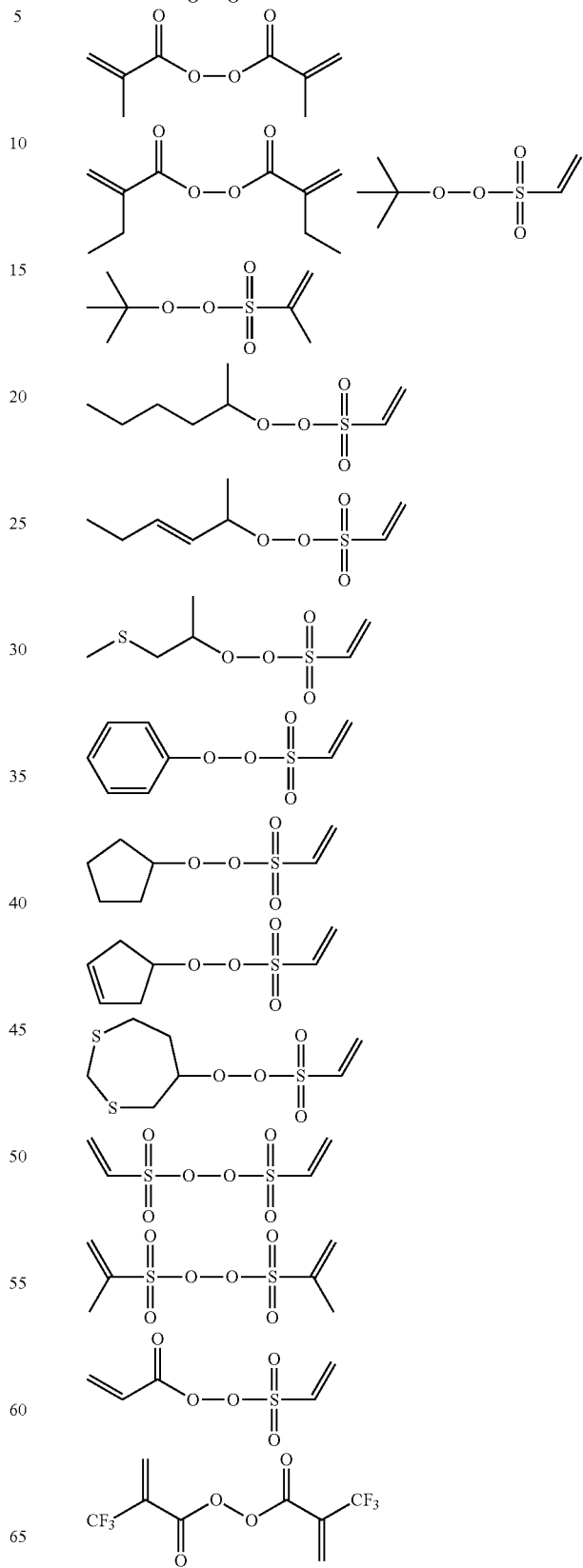

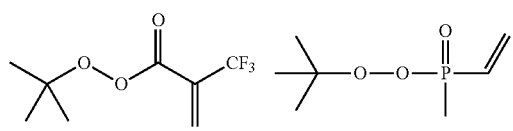
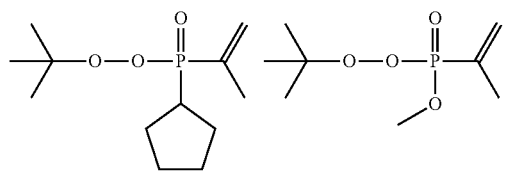
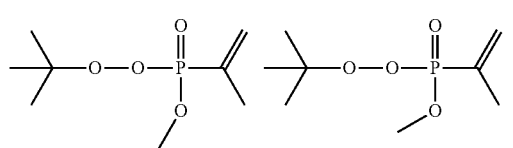
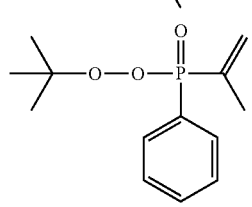
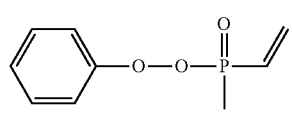
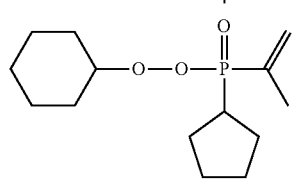
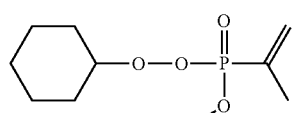
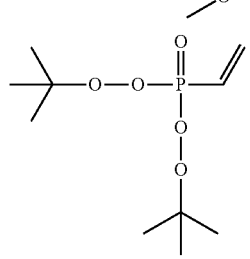
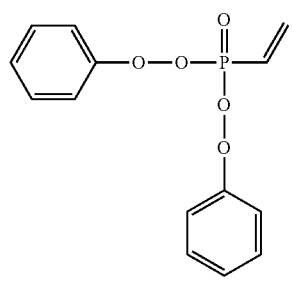

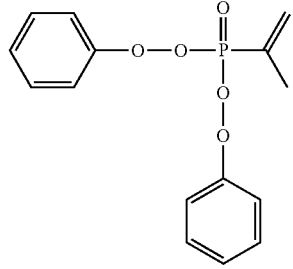
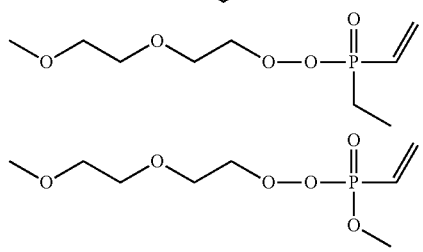
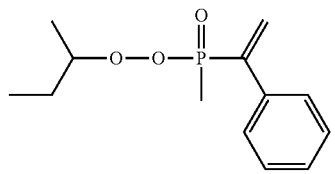
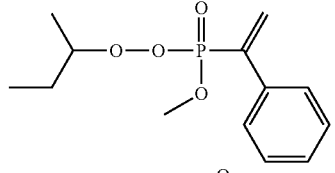
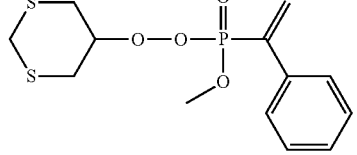
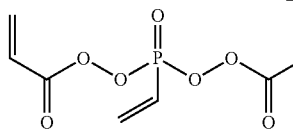
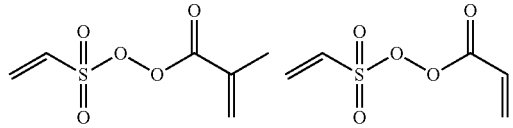

The compositions according to the invention are suitable in particular for use as dental material or for producing dental materials. For this, the compositions according to the invention contain a polymerizable binder which is preferably chosen from polyaddition resins and particularly preferably from radical polymerization resins. The polymerizable binder is also called polyreaction resin below, wherein polyreaction is the generic term for polymerization and polyaddition.

Known polymerization and polyaddition resins which as a rule are composed of a mixture of low-molecular or oligomeric monomers which contain one or more polyreactive groups can be used as polyreaction resins. Radically polymerizable resins come into consideration in particular in the case of polymerization resins. In the case of the polyaddition resins, thiol-ene resins are above all suitable. Both in the case of polymerization and polyaddition resins, the use of cross-linking polyreaction resins is preferred.

The use of radically polymerizable resins as binders is particularly preferred according to the invention. Quite particularly preferred are compositions which contain as radically polymerizable binder a mono- or multifunctional (meth)acrylate, an N-mono- or N-disubstituted (meth)acrylamide or a mixture thereof. Furthermore, such radically polymerizable binders are preferred which contain at least 50 wt.-%, particularly preferably at least 60 wt.-% and in particular at least 70 wt.-%, i.e. 70 to 100 wt.-% polyfunctional (meth)acrylates and/or polyfunctional (meth)acrylamides, wherein the percentages here relate to the mass of the polymerizable binder. By monofunctional (meth)acrylates or (meth)acrylamides are meant compounds with one, by polyfunctional (meth)acrylates or (meth)acrylamides compounds with two or more, preferably 2 to 4 (meth)acrylate or (meth)acrylamide groups. Polyfunctional monomers are also called cross-linking monomers.

Preferred mono- and multifunctional (meth)acrylates are methyl, ethyl, hydroxyethyl, hydroxypropyl, butyl, benzyl, 2-phenoxyethyl, glycidyl, tetrahydrofurfuryl or isobornyl (meth)acrylate, bisphenol-A-di(meth)acrylate, bis-GMA (an addition product of 2 mol methacrylic acid and 1 mol bisphenol-A-diglycidyl ether), addition products of 2 mol 2-hydroxyalkyl(meth)acrylate and 1 mol diisocyanates, such as e.g. hexamethylene diisocyanate or 2,2,4-trimethylhexamethylene diisocyanate, di-, tri- or tetraethylene glycol di(meth)acrylate, (meth)acrylate-terminated poly(ethylene glycol)s and poly(propylene glycol)s, trimethylolpropane tri(meth)acrylate, pentaerythritol tetra(meth)acrylate, as well as glycerol di- and tri(meth)acrylate, 1,4-butanediol di(meth)acrylate, 1,10-decanediol di(meth)acrylate, 1,12-dodecanediol di(meth)acrylate and dipentaerythritol monohydroxypenta(meth)acrylate. In addition, ethoxylated monomers, such as e.g. ethoxylated bis-GMA or ethoxylated trimethylolpropanetri(meth)acrylate are also suitable. Acrylates display a higher reactivity compared with the corresponding methacrylates, which manifests itself in a faster polymerization front. Further suitable radically polymerizable monomers are N-mono- or -disubstituted (meth)acrylamides, such as e.g. N-ethyl acrylamide, N,N-dimethacrylamide, N-(2-hydroxyethyl)acrylamide, N-methyl-N-(2-hydroxyethyl)acrylamide, N-ethyl methacrylamide or N-(2-hydroxyethyl)methacrylamide. In addition, vinyl- or allyl-group-containing monomers such as N-vinylpyrrolidone or allyl ether can be used as radically polymerizable binders. Corresponding cross-linking monomers, e.g. cross-linking pyrrolidones, such as e.g. 1,6-bis(3-vinyl-2-pyrrolidonyl)-hexane, or commercially available bisacrylamides, such as methylene or ethylene bisacrylamide, bismethacrylamides, such as e.g. N,N'-diethyl-1,3-bis(acrylamido)-propane, 1,3-bis(methacrylamido)-propane, 1,4-bis(acrylamido)-butane or 1,4-bis-(acryloyl)-piperazine can furthermore be used.

According to a further embodiment of the invention, compositions which use a polyaddition resin as binder are preferred. Thiol-ene resins which consist of mixtures of di- or multifunctional mercapto compounds and di- or multifunctional unsaturated monomers, in particular allyl or norbornene compounds, are preferred in particular as polyaddition resin. Di- or multifunctional means that the respective compounds contain 2 or more, preferably 2, 3 or 4, reactive allyl-, norbornenyl or mercapto groups. Here also, such binders are preferred which contain at least 50 wt.-%, particularly preferably at least 60 wt.-% and in particular at least 70 wt.-%, i.e. 70 to 100 wt.-% multifunctional compounds, wherein the percentages here relate to the mass of the polymerizable binder.

Examples of mono- or multifunctional mercapto compounds are o-, m- or p-dimercaptobenzene and esters of thioglycol or of 3-mercaptopropionic acid with ethylene, propylene or butylene glycol, hexanediol, glycerol, trimethylolpropane or pentaerythritol. Examples of di- or multifunctional allyl compounds are esters of allyl alcohol with di- or tricarboxylic acids, such as malonic, maleic, glutaric, succinic, adipic, sebacic, phthalic, terephthalic or gallic acid as well as mono- or trifunctional allyl ethers, such as e.g. diallyl ether, α,ω-bis[allyloxy]alkanes, resorcinol or hydroquinone diallyl ether as well as pyrogallol triallyl ether, or other compounds such as e.g. 1,3,5-triallyl-1,3,5-triazine-2,4,6-(1H,3H,5H)-trione, tetraallylsilane or tetraallylorthosilicate. Examples of di- or multifunctional norbornene compounds are Diels-Alder addition products of cyclopentadiene or furan with di- or multifunctional (meth)acrylates, as well as esters and urethanes of 5-norbornene-2-methanol or 5-norbornene-2-ol with di- or polycarboxylic acids, such as e.g. malonic, maleic, glutaric, succinic, adipic, sebacic, phthalic, terephthalic or gallic acid, or with di- or polyisocyanates, such as hexamethylene diisocyanate or its cyclic trimer, 2,2,4-trimethylhexamethylene diisocyanate, toluoylene diisocyanate or isophorone diisocyanate.

In addition, di- or multifunctional alkines can be reacted with the thiol components (thiol-ene resins).

In addition to the initiators of Formula I, the dental materials according to the invention preferably contain at least one further initiator for the radical polymerization and/or for the polyaddition. Thermal initiators and in particular photoinitiators are preferred as initiators for the radical polymerization. According to a particularly preferred embodiment, the invention therefore relates to compositions which, in addition to an initiator of Formula (I), contain radically polymerizable binder and a photoinitiator for the radical polymerization.

In particular, organic per compounds and azo compounds can be used as thermal initiators. Hydroperoxides, such as cumene hydroperoxide or tert.-butyl hydroperoxide, dialkyl peroxides, e.g. di-tert.-butyl peroxide or dicumene peroxide, diperoxiketals, such as 1,1-di(tert.-butylperoxi)cyclohexane or methyl ethyl ketone peroxide, per-acid esters, such as tert.-amylperoxiacetate, tert.-butyl perpivalate, tert.-butylper-2-ethylhexanoate or tert.-butyl perisobutyrate, diacyl peroxides, such as dibenzoyl peroxide, diisobutyryl peroxide, dioctanoyl peroxide, or dilauroyl peroxide, and peroxidicarbonates, such as e.g. diisopropyl peroxidicarbonate, di-n-butyl peroxidicarbonate or dicyclohexyl peroxidicarbonate are suitable as organic per compounds. Examples of suitable azo compounds are 2,2'-azobisisobutyronitrile, dimethyl-2,2'-azobisisobutyrate, 1,1'-azobis(1-cyclohexanenitrile), 2,2'-azobis(2,4,4-trimethylpentane) or azobis(2,4-dimethylvaleronitrile).

The quantity of gas-forming per compounds such as e.g. nitriles and peroxides is preferably less than 2 wt.-%, particularly preferably less than 1 wt.-%. Azo compounds are preferably used in a quantity of less than 1 wt.-%, particularly preferably less than 0.5 wt.-%. Per compounds which do not form gas upon thermal decomposition, such as e.g. persulphates, can be used in an amount of up to 5 wt.-%. All percentages relate to the overall mass of the material.

Preferred photoinitiators for compositions based on radically polymerizable resins as well as on thiol-ene polyaddition resins are the known Norrish type I radical UV photoinitiators (cf. J. P. Fouassier, Photoinitiation, Photopolymerization and Photocuring, Hanser Publishers, Munich, Vienna, New York 1995, 22 et seq.), such as benzil ketals, benzoin ethers, methyl thiophenyl morpholinoketones, dialkoxyacetophenones, hydroxyalkylphenylacetophenones, aminoketones or acylphosphine oxides. Suitable Norrish type II bimolecular UV photoinitiators are the systems benzophenone/amines, Michler's ketone/benzophenone and thioxanthone/amines (cf. J. P. Fouassier, J. F. Rabek (ed.), Radiation Curing in Polymer Science and Technology, Vol. III, Elsevier Applied Science, London and New York 1993, 189 et seq.). Suitable photoinitiators for the visible region (cf. J. P. Fouassier, J. F. Rabek (ed.), Radiation Curing in Polymer Science and Technology, Vol. III, Elsevier Applied Science, London and New York 1993, 228 et seq.) are e.g. bisacylphosphine oxides, but above all α-diketones such as 9,10-phenanthrenequinone, diacetyl, furil, anisil, 4,4'-dichlorobenzil and 4,4'-dialkoxybenzil and in particular camphorquinone. To accelerate the initiation by means of α-diketones, combinations with aromatic amines are preferably used. Redox systems which have already proved useful are combinations of camphorquinone with amines, such as N,N-dimethyl-p-toluidine, N,N-dihydroxyethyl-p-toluidine, ethyl 4-dimethylaminobenzoate or structurally related systems. Norrish type I photoinitiators, above all monoacyltrialkyl- or diacyldialkylgermanium compounds, such as e.g. benzoyltrimethylgermanium, dibenzoyldiethylgermanium or bis(4-methoxybenzoyl)diethylgermanium, are particularly suitable. Mixtures of the different photoinitiators can also be used, such as e.g. dibenzoyldiethylgermanium combined with camphorquinone and 4-dimethylaminoethylbenzoate.

To prevent a premature polyreaction, the compositions according to the invention preferably contain one or more polymerization or polyaddition inhibitors as stabilizers which make possible a storage stability of the material over approx. 2-3 years and can prevent an uncontrolled polyreaction. Phenols, such as hydroquinone monomethyl ether (MEHQ) or 2,6-di-tert.-butyl-4-methyl-phenol (BHT), which are effective only in the presence of oxygen and are preferably used in a concentration range from 200-2000 ppm, are used as so-called aerobic inhibitors for radical reaction resins and thiol-ene resins. Anaerobic inhibitors, such as e.g. phenothiazine, 2,2,6,6-tetramethylpiperidine-1-oxyl radical (TEMPO), iodine, copper(I) iodide, on the other hand, are effective in very small concentrations (10-50 ppm) even in the absence of oxygen. A polymerization takes place only when these additives are consumed. It is often also advantageous to use a mixture of aerobic and anaerobic inhibitors.

Furthermore, the polyreaction resins preferably also contain radically polymerizable, acid-group-containing adhesive monomers. Suitable acid-group-containing monomers are polymerizable carboxylic acids, such as maleic acid, acrylic acid, methacrylic acid, 2-(hydroxymethyl)acrylic acid, 4-(meth)acryloyloxyethyltrimellitic acid anhydride, 10-methacryloyloxydecylmalonic acid, N-(2-hydroxy-3-methacryloyloxypropyl)-N-phenylglycine and 4-vinylbenzoic acid. Examples of suitable phosphonic acid monomers are vinylphosphonic acid, 4-vinylphenylphosphonic acid, 4-vinylbenzylphosphonic acid, 2-methacryloyloxyethylphosphonic acid, 2-methacrylamidoethylphosphonic acid, 4-methacrylamido-4-methyl-pentyl-phosphonic acid, 2-[4-(dihydroxyphosphoryl)-2-oxa-butyl]-acrylic acid or 2-[4-(dihydroxyphosphoryl)-2-oxa-butyl]-acrylic acid ethyl- or -2,4,6-trimethylphenyl ester. Examples of suitable acid polymerizable phosphoric acid esters are 2-methacryloyloxypropyl mono- or dihydrogen phosphate, 2-methacryloyloxyethyl mono- or dihydrogen phosphate, 2-methacryloyloxyethylphenyl hydrogen phosphate, dipentaerythritol-pentamethacryloyloxyphosphate, 10-methacryloyloxydecyl-dihydrogen phosphate, phosphoric acid mono-(1-acryloyl-piperidine-4-yl)-ester, 6-(methacrylamido)hexyl dihydrogen phosphate and 1,3-bis-(N-acryloyl-N-propyl-amino)-propan-2-yl-dihydrogen phosphate. Examples of suitable polymerizable sulphonic acids are vinyl sulphonic acid, 4-vinylphenyl sulphonic acid or 3-(methacrylamido)propyl sulphonic acid.

The listed acid monomers are radically polymerizable and are therefore particularly suitable for combining with radically polymerizable binders. Preferred monomers are 4-(meth)acryloyloxyethyltrimellitic acid anhydride, 10-methacryloyloxydecylmalonic acid, 2-methacrylamidoethylphosphonic acid, 2-[4-(dihydroxyphosphoryl)-2-oxa-butyl]-acrylic acid ethyl- or -2,4,6-trimethylphenyl ester, 10-methacryloyloxydecyl-dihydrogen phosphate, 6-(methacrylamido)hexyl dihydrogen phosphate or 1,3-bis-(N-acryloyl-N-propyl-amino)-propan-2-yl-dihydrogen phosphate. Acid monomers and in particular the preferred acid monomers are preferably used in a quantity of 0 to 20 wt.-%, particularly preferably from 1 to 10, relative to the overall mass of the dental material.

In addition, the compositions according to the invention, in order to improve the mechanical properties or to adjust the viscosity, can be filled for example with organic or inorganic particles. The fillers preferably have an average particle size of 0.01 to 10 µm, particularly preferably from 0.02 to 5 µm. Preferred inorganic particulate fillers are amorphous spherical materials based on oxides, such as pyrogenic silica or precipitated silica, $ZrO_2$ and $TiO_2$ or mixed oxides of $SiO_2$, $ZrO_2$ and/or $TiO_2$ with an average particle diameter of 10 to 200 nm, mini fillers such as quartz, glass ceramic or glass powder with an average particle size of 0.01 to 1 µm as well as X-ray opaque fillers, such as ytterbium trifluoroide or nanoparticulate tantalum(V) oxide or barium sulphate, which preferably have an average particle size of from 10 to 200 nm.

In addition, the compositions used according to the invention can contain further additives, in particular solvents or corresponding solvent mixtures as well as flavourings, dyes, microbiocidal active ingredients, fluoride-ion-releasing additives, optical brighteners, plasticizers or UV absorbers.

Particularly preferred compositions according to the invention for use as dental material contain the following components:

a) 0.1 to 10 wt.-%, preferably 0.2-8 wt.-% and particularly preferably 0.5-5 wt.-% initiator according to Formula I;
b) 0.01 to 10 wt.-%, particularly preferably 0.1 to 3.0 wt.-% of one or more thermal initiators and/or photoinitiators, preferably photoinitiators,
c) 10 to 99 wt.-%, preferably 20 to 99 wt.-% and particularly preferably 25 to 98 wt.-% binder,
d) 0 to 85 wt.-%, particularly preferably 0 to 75 wt.-%, quite particularly preferably 0 to 60 wt.-% and in particular 0 to 40 wt.-% of one or more fillers,
e) 0 to 30 wt.-%, particularly preferably 0 to 20 wt.-% and quite particularly preferably 0 to 10 wt.-% stabilizers and/or additives.

Due to the different reactivity of the radically polymerizable monomers and polyaddition resins, the initiator according to Formula (I) is preferably used, depending on the binder used, in the following quantities:

Acrylate(s): 0.2-5 wt.-%, particularly preferably 0.5-2 wt.-%;
Acrylamide(s): 0.2-5 wt.-%, particularly preferably 0.5-2 wt.-%;
Methacrylate(s): 1-10 wt.-%, particularly preferably 2-5 wt.-%,
Thiol-ene resin(s): 1-10 wt.-%, particularly preferably 2-5 wt.-%.

All weight percentages relate to the overall mass of the composition if not stated otherwise. Single-component compositions are preferred according to the invention.

The quantity of initiator of Formula (I) and optionally further thermal initiators also varies with the quantity of fillers, solvents and other non-reactive components. If there is a large proportion of non-reactive components, a high initiator quantity is more likely chosen, whereas if the proportion of non-reactive components is small, smaller quantities of initiator are sufficient to effect a through-curing of the materials.

The compositions according to the invention are characterized due to their content of one or more initiators of Formula (I) in that they can be cured by frontal polymerization with reduced front temperature, with the result that the problems associated with high temperatures are avoided. The quantity of initiator of Formula (I) is preferably chosen such that the front temperature is between 40 and 100° C., preferably between 50 and 80° C.

The compositions according to the invention are particularly suitable as dental materials, in particular as prosthesis plastics, cements, composites, composite cements or filling composites, veneering materials and inlay materials.

The invention also relates to processes for producing dental or non-dental moulded bodies. For this, a composition according to the invention is first formed into the desired shape, for example through introduction into a suitable mould, and then through-cured, preferably by frontal polymerization. For example, today modern prosthesis plastics are often light-curing materials which display certain through-curing problems due to their layer thickness. Such prostheses are cured after shaping e.g. in a so-called light furnace, i.e. they are irradiated with light of a suitable wavelength and the polymerization reaction is thereby triggered. Here, the dental materials according to the invention can be used advantageously as the through-curing depth can be improved through the use of frontal polymerization.

A further subject of the invention is the use of initiators of Formula (I) to reduce the front temperature and/or to improve the through-curing depth upon frontal polymerization, in particular upon frontal polymerization of the above-defined compositions based on radically polymerizable binders. The use of the above-defined compounds of Formula (I) as initiators for frontal polymerization is likewise a subject of the invention.

The invention also relates to the use of compositions curable by front polymerization as dental material or for producing a dental material. The use of radical polymerizable compositions is preferred. These compositions preferably contain the above-named components, in particular in the defined quantities.

In addition to the dental application, the compositions according to the invention are also suitable for non-dental applications. Here, there may be named in particular industrial uses, such as e.g. sealing material for coils and printed circuit boards, casting compounds and sealing compounds as well as adhesives; surgical and medical uses, such as the sealing of medical equipment which contains electronic components; use in automobile manufacture, including the industrial embedding and sealing of various car parts; electronic applications in which secure and reliable seals are required, including the embedding of electronic components and parts. Use in the biomedical field and for the production of in vivo curable materials such as e.g. bone cements is also of interest.

The above-defined compositions which are optimized for dental purposes are suitable for non-dental applications. In addition, in general all radically polymerizable binders can be used for non-dental compositions. A good overview is given in: G. Webster, G. Bradley, C. Lowe, *A Compilation of Oligomers and Monomers Commercially Available for UV Today*, SITA Technology, London (2001). Preferred here are the compounds described in sections III ii) iii) iv). Oligomeric compounds from section I as well as monoacrylates from section III i) are preferably used only in small proportions (<30 wt.-%, preferably <10 wt.-%). In general, acrylates are preferred over methacrylates, wherein in particular such mixtures which generate a sufficient polymerization heat development are preferred. This is achieved e.g. by preferably taking acrylate-based monomers with a low molecular weight in order to keep the number of double bonds per gram and thus the exothermal activity as high as possible. Both inorganic and organic materials are suitable as fillers, wherein the quantity used is limited by the fact that the front temperature should not fall below the suitable range.

Specially suitable for non-dental applications are multifunctional acrylates which are selected from 1,6-hexanediol diacrylate, polyethylene glycol diacrylate, trimethylolpropane triacrylate, ethoxylated trimethylolpropane triacrylate, ditrimethylolpropane tetraacrylate and dipentaerythritol penta/hexaacrylates. According to a preferred embodiment, the multifunctional acrylate is trimethylolpropane triacrylate.

Non-dental compositions preferably likewise additionally contain a photoinitiator. Preferred photoinitiators are bis(2,4, 6-trimethylbenzoyl-phenyl phosphine oxide, 1-hydroxy-cyclohexyl-phenyl-ketone, 2,2-dimethoxy-1,2-diphenylethane-1-one and 2-methyl-1-[4-(methylthio)phenyl]-2-morpholinopropane-1-one.

Preferred fillers are clay and calcium carbonate.

Further preferred non-dental compositions are those which contain a liquid resin selected from cycloaliphatic epoxides and vinyl ethers and mixtures thereof with epoxypolyolefin ethers, at least one cationic photoinitiator, preferably one or more iodonium salts which form Lewis acids upon UV irradiation or upon heating, an activator for the photoinitiator, such as e.g. an alpha-hydroxy ketone, and an initiator according to Formula (I). If a cycloaliphatic epoxide is used as liquid resin, the composition preferably also contains a hydroxyl component which reacts upon UV irradiation with the epoxide, such as e.g. an alkyl alcohol. These compositions can furthermore contain plasticizers, pigments and dyes.

In cases in which a reduced front temperature is not required, the addition of initiators of Formula (I) can be omitted, i.e. the invention also relates to the use of compositions which contain the radically polymerizable binder and initiator for the radical polymerization, preferably a thermal initiator and/or a photoinitiator, as dental material or for producing a dental material. The above-defined components are particularly suitable as binders and initiators. In addition, the compositions can contain filler and one or more additives as stated above.

The use of frontal polymerization for curing dental materials is likewise a subject of the invention.

The invention is explained in more detail below by means of examples.

EMBODIMENT EXAMPLES

Example 1

Synthesis of tert.-butyl peracrylate (tBPA)

3.9 mmol tert.-butyl hydroperoxide (as 70% aqueous solution) was introduced into a round-bottomed flask and approx. 10,000 ppm MeHQ as inhibitor, dissolved in approx. 3 ml $H_2O$, added. 1 equivalent KOH (50%, aq.) was added dropwise slowly, then 12 equivalents NaCl added as 20% solution, accompanied by ice bath cooling. After 0.5 h stirring and cooling to −5° to 0° C., 1.1 equivalents acrylic acid chloride (contains 400 ppm phenothiazine as inhibitor) was added dropwise very slowly accompanied by vigorous stirring, after a further 3.5 h stirring at constant temperature approx. 15 ml methylene chloride was added and the reaction solution was extracted with NaHCO$_3$ solution. After drying over anhydrous Na$_2$SO$_4$ and filtering, approx. 10,000 ppm hydroquinone monomethylether (MEHQ) was added once again as inhibitor to the organic phase. The product was purified by means of flash column chromatography (CH$_2$Cl$_2$). As the inhibitor was separated off upon purification, a further 1,000 ppm MeHQ was added. By careful suction, the solvent was removed without major product losses and approx. 200 mg (33% yield) of the tert.-butyl peracrylate was obtained as yellowish liquid.

$^1$H-NMR (CDCl$_3$), δ (ppm): 6.54-6.44 (dd, 1H, C=CH$_2$); 6.18-6.04 (m, 1H, CH=CH$_2$); 5.93-5.87 (dd, 1H, C=CH$_2$); 1.34 (s, 9H, —C(CH$_3$)$_3$).

$^{13}$C-NMR (CDCl$_3$), δ (ppm): 164.3 (C=O); 132.0 (—CH=CH$_2$); 124.3 (—CH=CH$_2$); 83.8 (—C(CH$_3$)$_3$); 26.2 (—C(CH$_3$)$_3$).

Example 2

Thermal stability of tert.-butyl peracrylate

The thermal stability of hexanediol dimethacrylate (HDDMA) mixtures of various per compounds which contained 167 μmol/g per compound was investigated using DSC. Heating to 200° C. was carried out at a heating rate of 1° C./min in order to determine the temperature at which sufficient peroxide decomposes in order to initiate a polymerization (cf. Tab. 1). The weighed-in quantity per DSC pan was approx. 15 mg, a container with Al$_2$O$_3$ was used as "comparison sample". In addition to the tert.-butyl peracrylate (tBPA) from Example 1, propionic acid (tBPP) and isobutyric acid-tert.-butyl perester (tBPiB) were investigated as per compound. The initiation temperature of pure HDDMA was likewise determined. The results are summarized in Table 1.

Table 1 shows that the addition of tBPA to HDDMA clearly reduces the starting temperature of the polymerization (ΔT≈60°), i.e. that tBPA is active as initiator.

TABLE 1

Starting temperature of the polymerization of HDDMA initiated by various per compounds

| per compound | Starting temperature (° C.) |
|---|---|
| none | 163 |
| isobutyric acid-tert.-butyl perester (tBPiB)*) | 79.5 |
| propionic acid-tert.-butyl perester (tBPP)*) | 98.5 |
| tert.-butyl peracrylate (tBPA) | 103.5 |

*)Comparison example

The results further show a lower starting temperature for the isobutyric acid perester tBPiB which represents a model substance for the polymerized-in peracrylate tBPA and demonstrates a destabilization of the peracrylate used by the radical-induced polymerization. The less branched tBPP displays a higher starting temperature than tBPiB. It can be concluded from the results that in the case of tBPA the frontal polymerization takes place at a polymerization front temperature of approx. 80° C.

Example 3

Storage stability of tert.-butyl peracrylate

To be able to assess the storage stability of tert.-butyl peracrylate (tBPA), formulations of N-acryloyl morpholine (NAM) with 1 μmol/g bis(4-methoxybenzoyl)diethylgermanium as photoinitiator and varying quantities of tBPA (approx. 0.1% or 1%, corresponding respectively to 4.71 mmol/g and 47.1 mmol/g) were stored at 43° C. for 8 weeks and the viscosity of the mixture then measured. The results are shown in Table 2. After 8 weeks, the same viscosity resulted within the framework of measuring accuracy, which demonstrates the good storage stability of tBPA at room temperature. No polymerization was observed.

The results demonstrate a high storage stability of tert.-butyl peracrylate-containing resins at room temperature.

TABLE 2

Viscosity of tBPA in NAM, shear rate 102 s$^{-1}$; storage time 8 weeks

| Quantity of tBPA [%] | η [mPa · s] |
|---|---|
| — | 11.0 |
| 0.1% | 10.9 |
| 1% | 22.2 |

Example 4

Frontal Polymerization (FP) of Resin Mixtures

Irradiation tests with mixtures of trimethylolpropane triacrylate (TMPTA) with the UV photoinitiator (5% Darocur 1173) and various quantities of tert.-butyl peracrylate (tBPA) were carried out in sealed Pasteur pipettes accompanied by broad-band irradiation (5 sec, 320-500 nm, light intensity=3 W/cm$^2$). The 450 mg of the formulations poured in for the measurements corresponded to a fill level of approx. 14 mm. The pipette was irradiated from below, and the thickness of the polymerized layer was measured. The results are shown in Table 3.

Acryl acid-tert.-butyl ester was used as comparison monomer. It does not contain a reactive peroxide group and thus does not trigger frontal polymerization. The thickness of the polymerized layer is identical to the layer thickness which was achieved without additive. The addition of 1 wt.-% tBPA led to a clear increase in the layer thickness, which demonstrates that a frontal polymerization takes place here. To accurately measure the layer thickness, the test was repeated with a larger quantity of polymerizable composition. A layer thickness of 52 mm was measured, which is ten times that of the comparison example. The addition of just 0.2 wt.-% tBPA also already resulted in a clear increase in the layer thickness (approx. 60-70%).

TABLE 3

FP results in TMPTA

| Additive [%] | Layer thickness (mm) |
|---|---|
| — | 4-5 |
| acrylic acid-tert.-butyl ester 1%*) | 4-5 |
| tBPA 1% | 13** |
| tBPA 0.2% | 7-8 |
| tBPA 1% | 52*** |
| 25% OX-50 | 4-5 |
| 25% OX-50 + tBPA 1%** | 12 |

*)comparison example
**whole monomer cured
***1 g fill quantity

In a second series of tests, a mixture was used which also contained 25 wt.-% filler (Aerosil OX-50, Degussa, SiO$_2$ with a primary particle size of 40 nm). A cured layer of 12 mm resulted with 1% tBPA, and of only 4-5 mm without tBPA.

The results demonstrate a frontal polymerization with resin systems which contain a sufficient quantity of the peracrylate tBPA, wherein filled systems also result in a frontal polymerization. Dentures for example can be produced by frontal polymerization with such formulations.

The invention claimed is:

1. Polymerizable composition, comprising:
   (a) 0.1 to 10 wt.-% initiator according to the following Formula I:

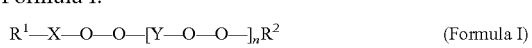  (Formula I)

in which
   $R^1$=is H, a linear, branched or cyclic aliphatic $C_1$-$C_{20}$ radical, which can contain one or more multiple bonds and/or one or more heteroatoms selected from O, S and —$NR^5$—, an aromatic $C_6$-$C_{14}$ radical or a combination of one such aliphatic and one such aromatic radical or has one of the meanings given for $R^2$;
   $R^5$=is H, phenyl or $C_1$-$C_9$ alkyl;
   X=is —CO— or is absent;
   $R^2$ is —CO-M, —$SO_2$-M or —P(=O)(-M)(—$R^3$);
   $R^3$=is R', —OR', or —OO(CO)$_m$R', wherein R' is H, a linear, branched or cyclic aliphatic $C_1$-$C_{20}$ radical, which can contain one or more multiple bonds and/or one or more heteroatoms selected from O, S and N, an aromatic $C_6$-$C_{14}$ radical or a combination of such an aliphatic and such an aromatic radical, and m is 0 or 1;
   M=is —CH=$CH_2$ or —C($R^4$)=$CH_2$;
   $R^4$=is a $C_1$-$C_{10}$ alkyl radical or a $C_3$-$C_8$ cycloalkyl radical, wherein these radicals can contain one or more S or O atoms, a phenyl radical or benzyl radical, wherein the named radicals can be halogenated, —F, —Cl or —Br;
   Y=is a bivalent, linear, branched or cyclic aliphatic $C_1$-$C_8$ radical; and
   n=is 0, 1, or 2,
   (b) 0.01 to 10 wt.-% photoinitiatior
   (c) 10 to 99 wt.-% polymerizable binder,
   (d) 0 to 85 wt.-% filler, and
   (e) 0 to 30 wt.-% stabilizers and/or additives, relative in each case to the overall mass of the composition.

2. Composition according to claim 1, in which at least one of the variables of Formula I has one of the following meanings:
   $R^2$=is H, a linear, branched or cyclic aliphatic $C_1$-$C_6$ radical, which can contain a multiple bond and/or one or more heteroatoms selected from O and S, an aromatic $C_6$-$C_{10}$ radical or a combination of one such aliphatic and one such aromatic radical or has one of the meanings given for $R^2$;
   X=is —CO— or is absent;
   $R^2$=is —CO-M, —$SO_2$-M or —P(=O)(-M)(—$R^3$);
   $R^3$=is R', —OR' or —OO(CO)$_m$R', wherein R' is H, a linear, branched or cyclic aliphatic $C_1$-$C_6$ radical, an aromatic $C_6$-$C_{10}$ radical or a combination of one such aliphatic and one such aromatic radical, and m is 0 or 1;
   M=is —CH=$CH_2$ or —C($R^4$)=$CH_2$;
   $R^4$=is a $C_1$-$C_2$ alkyl radical, —F, —Cl, —Br, —$CF_3$ or a phenyl radical;
   Y=is a bivalent, linear, branched or cyclic aliphatic $C_1$-$C_8$ radical; and
   n=is 0, 1 or 2.

3. Composition according to claim 1, which contains a radically polymerizable binder which is selected from mono- or multifunctional (meth)acrylates, N-mono- or N-disubstituted (meth)acrylamides or a mixture thereof.

4. Composition according to claim 1, which contains as binder a mixture of mono- and/or multifunctional mercapto compounds and di- and/or multifunctional unsaturated monomers (thiol-ene resin).

5. Composition according to claim 1, which additionally contains at least one stabilizer.

6. Composition according to claim 1, which additionally contains at least one additive which is selected from solvents, flavourings, dyes, microbiocidal active ingredients, fluoride-ion-releasing additives, optical brighteners, plasticizers or UV absorbers.

7. Composition according to claim 1, which contains
   acrylate(s) as binder and 0.2-5 wt.-% initiator of Formula (I) or
   acrylamide(s) as binder and 0.2-5 wt.-% initiator of Formula (I) or
   methacrylate(s) as binder and 1-10 wt.-% initiator of Formula (I) or
   thiol-ene resin(s) as binder and 1-10 wt.-% initiator of Formula (I).

8. Composition according to claim 1 for use as dental material.

9. Process for producing moulded bodies, in which a composition according to claim 1 is cured by frontal polymerization.

10. A method of using the polymerizable composition according to claim 1, that is curable by front polymerization for producing a dental material.

11. A method, according to claim 10, using frontal polymerization for curing dental materials.

12. A method of using the initiator of Formula (I) of claim 1 for an initiator for frontal polymerization.

* * * * *